United States Patent
Lee et al.

(10) Patent No.: US 8,092,987 B2
(45) Date of Patent: Jan. 10, 2012

(54) MUCOSA TISSUE PRESERVED WITH HEATING AND HYDROGEN PEROXIDE OR PHOSPHORIC ACID

(75) Inventors: John H. Lee, Olathe, KS (US); Joseph D. Hahn, Kansas City, MO (US); Robert C. Musser, Shawnee, KS (US)

(73) Assignee: Land O'Lakes Purina Feed, LLC, Arden Hills, MN (US)

( * ) Notice: Subject to any disclaimer, the term of this patent is extended or adjusted under 35 U.S.C. 154(b) by 950 days.

(21) Appl. No.: 11/646,660

(22) Filed: Dec. 28, 2006

(65) Prior Publication Data

US 2007/0105190 A1    May 10, 2007

Related U.S. Application Data

(62) Division of application No. 09/392,243, filed on Sep. 9, 1999, now Pat. No. 7,157,221.

(51) Int. Cl.
*A01N 1/00* (2006.01)
*A61K 35/37* (2006.01)

(52) U.S. Cl. ............ 435/1.1; 424/550; 424/551

(58) Field of Classification Search .......... None
See application file for complete search history.

(56) References Cited

U.S. PATENT DOCUMENTS

| | | | |
|---|---|---|---|
| 2,406,249 A | 8/1946 | Parfentjev | |
| 3,640,725 A | 2/1972 | Sherba et al. | |
| 3,857,966 A | 12/1974 | Feldman et al. | |
| 3,912,822 A | 10/1975 | Yokotsuka et al. | |
| 3,914,436 A | 10/1975 | Nakadai et al. | |
| 4,100,024 A | 7/1978 | Adler-Nissen | |
| 4,145,451 A | 3/1979 | Oles | |
| 4,275,166 A | 6/1981 | McCollough et al. | |
| 4,324,805 A | 4/1982 | Olsen | |
| 4,427,658 A | 1/1984 | Maubois et al. | |
| 4,438,100 A | 3/1984 | Balslev et al. | |
| 4,757,007 A | 7/1988 | Satoh et al. | |
| 4,812,173 A * | 3/1989 | Tsao et al. | 134/27 |
| 5,094,946 A | 3/1992 | Taylor et al. | |
| 5,262,307 A | 11/1993 | Savolainen | |
| 5,356,637 A | 10/1994 | Loosen et al. | |
| 5,607,840 A | 3/1997 | Van Gorp et al. | |
| 5,663,058 A | 9/1997 | Miyazaki et al. | |
| 6,666,892 B2 | 12/2003 | Hiles et al. | 623/23.72 |

FOREIGN PATENT DOCUMENTS

GB    992201    5/1965

OTHER PUBLICATIONS

Baldry et al., "The bacericidal, fungicidal and sporicidal properties of hydrogen peroxide and peracetic acid", J. Applied Bacteriology 54 : 417-423 (1983).*
http://www.vh.org/adult/provider/anatomy/MicroscopicAnatomy/Section10/Plate10192.html.

* cited by examiner

*Primary Examiner* — Sandra Saucier
(74) *Attorney, Agent, or Firm* — Dorsey & Whitney LLP; Devan V. Padmanabhan

(57) ABSTRACT

A process for hydrolyzing products with enzymatic activity remaining in peptone solutions after mucosa hydrolysis is provided along with a process for preserving mucosa tissue. Broadly, the processes are carried out by hydrolyzing mucosa tissue according to conventional heparin manufacturing processes wherein an excess quantity of proteolytic enzymes is used. The resulting peptone solution is then contacted with proteins or protein-containing materials in order to hydrolyze the proteins. In another embodiment, mucosa tissue is preserved by mixing it with a preserving agent selected from the group consisting of hydrogen peroxide and phosphoric acid. The product preserved by hydrogen peroxide is low in ash, stable for at least a week, and has a reduced odor.

5 Claims, No Drawings

US 8,092,987 B2

MUCOSA TISSUE PRESERVED WITH HEATING AND HYDROGEN PEROXIDE OR PHOSPHORIC ACID

CROSS-REFERENCE TO RELATED APPLICATION

This is a divisional application of U.S. Ser. No. 09/392,243, entitled "PROCESSES FOR MAKING PROTEIN HYDROLYSATES FROM ANIMAL PEPTONE AND FOR PRESERVING MUCOSA, filed on Sep. 9, 1999.

BACKGROUND OF THE INVENTION

1. Field of the Invention

The present invention is broadly concerned with processes for utilizing the enzymatic activity remaining in peptone solutions for carrying out various hydrolysis processes, as well as preserved mucosa tissue products and methods for preserving these products. More particularly, the mucosa tissue is hydrolyzed by conventional processes with an excess quantity of enzymes to yield a product comprising heparin (which is preferably extracted) and a peptone solution. A protein-containing material (e.g., soybeans, animal liver) is then hydrolyzed using the enzymatic activity remaining in the peptone solution. In another embodiment, the mucosa tissue is preserved by mixing the tissue with a preserving agent selected from the group consisting of hydrogen peroxide and phosphoric acid to yield a preserved product. The mucosa product preserved by hydrogen peroxide has a low ash count and reduced odor.

2. Description of the Prior Art

Peptone is a hydrolysate mixture derived from the mucosa tissue of swine, cattle, and other animals. Peptone is produced by hydrolyzing mucosa tissue with proteolytic enzymes to produce a digest solution containing, among other things, protein hydrolysates (i.e., peptone) and heparin. The heparin, which has great commercial value, is then extracted from the digest solution, typically by anion exchange resins. These processes and the resulting products have been described in U.S. Pat. No. 5,607,840 and GB 992,201, incorporated by reference herein.

When hydrolyzing mucosa tissue, large quantities of proteolytic enzymes are used in order to increase the heparin yield. For example, during mucosa hydrolysis, proteolytic enzymes are typically added at a rate of about 1-1.5 g of enzyme per kg of mucosa tissue. This is equivalent to about 13-20 g of enzyme per kg of protein present in the tissue as compared with about 0.2-3 g of enzyme per kg of protein utilized in other hydrolysis processes. Such large quantities of enzymes increase the costs of carrying out these processes and results in a substantial amount of enzymatic activity remaining after these processes have concluded. This activity is then deactivated by lowering the pH of the product (which is reversible) or by irreversibly denaturing the enzyme with heat. There is a need for a process which would provide commercially viable uses for this excess enzymatic activity.

There are numerous protein-containing materials which are hydrolyzed for various purposes which could benefit from this excess enzymatic activity. For example, soybeans are an inexpensive source of essential amino acids. However, anti-nutritional factors such as protease inhibitors and antigenicity are also present in soybeans. These factors can be substantially reduced by hydrolyzing the soybean proteins. Similarly, whey proteins are an important source of proteins for young animals, but whey proteins have a drawback in that they may cause allergic reactions. This risk of reaction can be reduced by hydrolyzing the whey proteins. Finally, enzymatic hydrolysis processes have other useful purposes, including reducing the viscosity of blood products, increasing the bioavailability of feed-grade meat isolates, and increasing the quantity of soluble materials which can be extracted from by-products such as fish offal.

On a dry basis, typical peptone derived from heparin production processes includes about 50-55% by weight crude protein and about 20-30% by weight ash. Due to this protein content, peptone is commonly used as a nutritional supplement for animals. However, currently available peptone suffers from two disadvantages—a high ash level and an unappealing flavor. High ash contents in peptone have been shown to adversely affect animal weight gain (see e.g., *Journal of Dairy Science*, Vol. 75(1):267 (1992)). These high levels are predominantly caused by the current mucosa preservation methods wherein sodium metabisulfite or calcium propionate is added to the mucosa product or wherein the pH of the product is lowered. There is a need for a mucosa preservation method which is effective yet does not generate high levels of ash in the resulting peptone solution, thus reducing the unappealing flavor in peptone.

SUMMARY OF THE INVENTION

The instant invention overcomes the problems of the prior art by providing improved mucosa tissue preservation methods as well as methods of utilizing the enzymatic activity remaining in the peptone solution after mucosa hydrolysis and heparin extraction.

Broadly, the enzymatic activity in peptone solution can be utilized to hydrolyze other protein-containing materials, either as the sole source of enzymatic activity or in conjunction with another enzyme for either supplementing the available activity or hydrolyzing a constituent other than protein (e.g., fat). These processes comprise first hydrolyzing a quantity of mucosa tissue (which inherently contains proteins) with at least one proteolytic enzyme so as to yield a hydrolyzed product which includes heparin and peptone. Preferably the heparin is then extracted by conventional techniques (e.g., by anion exchange resins) leaving the peptone solution which includes hydrolysates, salts, and possibly phosphorous. While in prior art processes the enzymatic activity of the peptone solution is deactivated by the application of heat, this is not necessary with the inventive processes. Rather it is preferred that the remaining enzymatic activity in the peptone solution be used for further hydrolysis processes.

In order to be commercially worthwhile, the peptone solution should retain at least about 30%, preferably at least about 40%, and more preferably at least about 50% of the enzymatic activity of the starting proteolytic enzymes used to hydrolyze the mucosa as determined by the enzymatic assay utilized by the manufacturer of the enzyme. This solution can then be used to hydrolyze other proteins by simply contacting the peptone solution with the proteins under the appropriate hydrolyzing conditions so as to yield a final hydrolyzed product. The peptone solution and proteins or protein-containing material should be mixed in quantities such that the level of peptone solution utilized is less than about 50% by weight on a solids basis, and preferably from about 15 to 30% by weight on a solids basis, based upon the total solids weight of both the protein or protein-containing material and the peptone solution taken as 100% by weight. Examples of protein-containing materials which can be hydrolyzed with the enzymatic activity remaining in a peptone solution include animal liver, animal viscera, wheat, soybeans, products comprising blood, whey products, animal offal, meat isolates and mixtures of the foregoing. The quantity of peptone solution utilized depends upon the enzymatic activity, product combination, nutritional factors, and other factors.

While the above processes utilize the peptone solution remaining immediately after heparin formation and extraction, it will be appreciated that these processes will also work on peptone solution purchased from peptone manufacturers provided the enzymatic activity in the solution was deactivated by pH adjustment rather than by the irreversible denaturation of the enzymes by heat. In these instances, it would first be necessary to reactivate the enzymatic activity by adjusting the pH of the acidic peptone solution to at least about 6.5, and preferably at least about 7.5. The pH-adjusted peptone solution would then simply be contacted with the proteins or protein-containing material as described above.

Furthermore, while the foregoing processes were described with respect to peptone solutions hydrolyzed from mucosa, other hydrolyzation products can also be used so long as they are obtained by processes using an excess quantity of proteolytic enzymes (e.g., at least about 10 g of enzyme per kg of protein). The remainder of the process would be carried out as described above.

In another embodiment, mucosa tissue can be preserved by contacting the tissue with a preserving agent selected from the group consisting of hydrogen peroxide and phosphoric acid. In applications where phosphoric acid is utilized as the preserving agent, the preservation process is carried out by simply mixing the phosphoric acid with the mucosa tissue in sufficient quantities to maintain the tissue pH at a level of about 2-4, and preferably about 2.5-3. The mixing is carried out by mechanical agitation and under ambient conditions. The use of phosphoric acid has the benefit that it can eliminate the need for supplemental dietary phosphorous by increasing the phosphorous content in the mucosa tissue product, and thus in the resulting peptone solution, to a level of about 4% by weight on a dry basis.

In applications where hydrogen peroxide is utilized as the preserving agent, it is preferably to first heat (such as by direct steam injection) the mucosa tissue to a temperature of from about 50-105° C., and preferably from about 65-75° C. prior to mixing the hydrogen peroxide with the mucosa tissue. Only very small quantities of hydrogen peroxide are required to preserve the mucosa tissue. Therefore, the hydrogen peroxide should be mixed at a level of less than about 1% by weight hydrogen peroxide, and preferably less than about 0.5% by weight hydrogen peroxide, based upon the total weight of the mucosa tissue taken as 100% by weight.

The quantity of hydrogen peroxide remaining in the final preserved product, without any treatment to remove excess hydrogen peroxide, is less than about 0.04% by weight, and preferably less than about 0.01% by weight, based upon the total weight of the preserved product taken as 100% by weight, and would even more preferably be determined to be undetectable by standard methods conventionally used in the art. If there is hydrogen peroxide remaining after the process, it can be removed by peroxidase hydrolysis processes or other known methods.

The preserved mucosa tissue has an ash content of less than about 10% by weight, and preferably less than about 7% by weight, based upon the total weight of the preserved tissue taken as 100% by weight. Those skilled in the art will appreciate that this low ash content substantially reduces the poor flavor generally associated with peptone and peptone-supplemented products derived from mucosa hydrolysis processes. Finally, the preserved mucosa tissue products have very low bacterial counts. For example, the products will have a standard plate count of less than about 20,000 cfu/g, and preferably less than about 5,000 cfu/g about 7 days after the tissue is treated with the preserving agent. The Coliform count will be less than about 10 cfu/g, and preferably less than about 3 cfu/g about 7 days after the tissue is treated with the preserving agent. Also, the *E. Coli* count of the product will be less than about 10 cfu/g and preferably less than about 3 cfu/g about 7 days after the tissue is treated with the preserving agent. As a result of these low counts, the unappealing odor of mucosa tissue is substantially reduced. This process is particularly useful for preserving mucosa tissue which will not be hydrolyzed or otherwise processed for a number of days.

DETAILED DESCRIPTION OF THE PREFERRED EMBODIMENTS

Examples

The following examples set forth preferred methods in accordance with the invention. It is to be understood, however, that these examples are provided by way of illustration and nothing therein should be taken as a limitation upon the overall scope of the invention.

Example 1

Mucosa Preservation with $H_2O_2$ Followed by Hydrolysis

Porcine mucosa was heated with steam injection under agitation to 73° C. The steam was stopped, and the solution was mixed for 13 minutes. Hydrogen peroxide (0.5% of pure hydrogen peroxide, which is equivalent to 1.5% of 34% hydrogen peroxide) was added to the solution followed by mixing for 10 minutes. The color of the solution changed so that it was similar to the color of a whey protein solution. The solution was analyzed to determine whether there was any hydrogen peroxide remaining. This was carried out by adding 0.01 M $KmnO_4$ to the diluted solution (1:150) and observing whether a color change took place. This test indicated that there was no hydrogen peroxide remaining in the product. The analytical data of the solution was as follows: protein (76% on a dry basis), ash (7.5% on a dry basis) and moisture (86% by weight). The micro counts after 7 days at regular storage conditions were: on SPC—300 cfu/g; *Salmonella*—negative/25 g; *E. Coli*—3 cfu/g; and Coliforms—3 cfu/g. After 20 days at regular storage conditions, the counts were: SPC—600 cfu/g; *Salmonella*—negative/25 g; *E. Coli*—3 cfu/g; and Coliforms—3 cfu/g. The mucosa solution had no off-odor after 7 days.

Six days later, the above porcine mucosa was transferred to a stainless steel container. A commercially available bacterial alkaline protease enzyme having a minimum activity of 580,000 DU/g was added to the solution at a rate of 1 g of enzyme per kg of mucosa. The solution was heated in a water bath at a temperature of 55° C. The pH of the solution was adjusted to 9.2 with sodium hydroxide. The viscosity of the solution was significantly reduced after about 30 minutes of hydrolysis, indicating that hydrolysis was taking place. The complete hydrolysis process lasted 5 hours after which the solution was divided into three portions. The pH of the first portion of the solution was adjusted to 5.0 with 6 N HCl as is conventional in the prior art preservation processes. The second portion of the solution was treated by the addition of hydrogen peroxide (0.2% of pure hydrogen peroxide, which is equivalent to 0.6% of 34% hydrogen peroxide) according to the instant invention. The third portion of the solution was used for heparin extraction with an anion ion exchange resin. The analytical data of the peptone after heparin extraction were as follows: protein (66.2% on a dry basis); ash (13.6% on a dry basis); and moisture (86% by weight).

Enzyme activity was determined by under the different processing conditions. The results were as follows:

| Process | % Activity Remaining |
|---|---|
| After 5 hours hydrolysis w/mucosa | 57.9 |
| After treatment with HCl to a pH of 5 | 37.8 |
| After treatment with 0.2% $H_2O_2$ | 9.9 |

Example 2

Mucosa Preservation with Phosphoric Acid Followed by Hydrolysis

Phosphoric acid (75%) was added to porcine mucosa under mixing until the pH of the mixture was about 2.8. The micro counts after 7 days at regular storage conditions were: on SPC—3×10$^5$ cfu/g; *Salmonella*—negative/25 g; *E. Coli*—<3 cfu/g; and Coliforms—<3 cfu/g. There was some off-odor after 5 days at regular storage conditions. After 5 days, a commercially available bacterial alkaline protease enzyme having a minimum activity of 580,000 DU/g was added to the solution at a rate of 1 g of enzyme per kg of mucosa. The solution was heated to 55° C. in a water bath, followed by adjustment of the solution pH to about 9.2 with sodium hydroxide. After just one-half hour of hydrolysis the viscosity of the solution was significantly reduced, indicating that the proteins were being hydrolyzed to peptides. Hydrolysis was carried out for 5 hours after which 6 N HCl was added to the solution to adjust the pH to 7. The heparin was then extracted with an anion ion exchange resin. The analytical data of the solution were: protein (50.6% on a dry basis); moisture (80.6%); and ash (29.7% on a dry basis).

Example 3

Peptone and Chicken Liver

Peptone solution (obtained from a heparin manufacturer and having 9% protein on a dry basis and 84% by weight moisture at a pH 5.4 after heparin extraction) was mixed with chicken liver and tap water at a ratio of 1:1.5:1.5 (peptone solution:chicken liver:water-weight basis). The mixture was blended with a kitchen blender for 2 minutes. Sodium hydroxide was added to adjust the pH to 8.0 while agitating the solution. The solution was then heated to 55° C. in a water bath, and the temperature was maintained for 3 hours. The pH was checked every 30 minutes during this 3 hour period, and sodium hydroxide was added as necessary to adjust the pH to 8.0. After one hour of the 3 hour period, the solution was blended with the kitchen blender for 1 minute. At the end of the 3 hour period, the solution was heated to 88° C. for 5 minutes to inactivate the enzymes followed by drying at 90° C. overnight. The resulting solid was ground into a light-yellowish color powder which had a liver flavor. The analytical data of the dried product in % by weight of dried product were as follows: protein (59.1%); moisture (4.4%); ash (17.6%); and fat (16.8%). The analytical data of the peptone powder (given as % by weight, based upon the weight of all components in the product) were as follows: protein (52.8%); moisture (12.4%); ash (25.9%); and fat: (10.6%).

Under the same processing conditions, chicken liver without peptone and chicken liver with both peptone and a commercially available bacterial alkaline protease enzyme having a minimum activity of 580,000 DU/g added at a rate of 0.5 g of enzyme per kg of solid were also processed. A comparison of the three samples is shown below. The lowered viscosity indicated that the proteins were hydrolyzed to peptides, even in the sample where no enzyme was used to supplement the enzymatic activity remaining in the peptone solution.

| Samples | Viscosity | At 88° C. for 5 minutes |
|---|---|---|
| Liver/water | very high | large pellet formed |
| Liver/peptone/water | low | small pellet formed |
| Liver/peptone/water/enzyme | low | no pellet |

Example 4

Peptone and Soybean Meal

Peptone solution was obtained from a heparin manufacturer. The peptone solution had 9% protein on a dry basis and 84% by weight moisture at a pH 5.4. Dry soybean meal was mixed with tap water to form a dispersion having a 10% solids (w/w) content. The peptone solution and soybean meal solution were then mixed at a ratio of 1:2 (peptone solution: soybean meal solution-volume basis). Sodium hydroxide was added to change the pH of the resulting solution from 5.7 to 8.0 with the solution being agitated during the sodium hydroxide addition. A commercially available bacterial alkaline protease enzyme having a minimum activity of 580,000 DU/g was added to the solution at a rate of 1 g of enzyme per kg of solid. The solution was then heated to 55° C. by a water bath, and this temperature was maintained for a time period of about 2.5 hours. The solution was homogenized for 1 minute at 5,000 rpm every 45 minutes during this 2.5 hour period. The pH was checked approximately every 30 minutes during this 2.5 hour period, and sodium hydroxide was added as necessary to adjust the pH to 8.0. The solution was heated to 90° C. for 5 minutes to inactivate the enzymes followed by filtering with a nylon bag having 850 µm holes. The residue which did not pass through the nylon bag was then dried at 100° C. for 15 hours. The dried residue was weighed, and it was determined that the ratio of the residue against the dry soybean meal was 4%, indicating that 96% of soybean meal had been solubilized. There was a small quantity of residue left in the nylon bag which could not be removed, thus the recovery percentage might have been slightly lower than 96%. The solution which passed through the nylon bag was dried in an oven overnight at 100° C. The resulting solid was ground into a light-colored powder which had a mild flavor. The analytical data were as follows: protein (48.8%); moisture (6.6%); and fat (2.4%).

Under the same processing conditions, soybean meal samples both without and with peptone were processed. A comparison of the three samples is shown below. The lower viscosity indicated that the protein was hydrolyzed to peptides, even in the sample where no additional enzyme was added to supplement the enzymatic activity remaining in the peptone solution.

| Samples | Liquid Forms | Viscosity |
|---|---|---|
| Soybean meal/water | slurry | high |
| Soybean meal/peptone/water | solution | low |
| Soybean/peptone/water/enzyme | solution | low |

Example 5

Peptone and Blood Products

Peptone solution (obtained from a heparin manufacturer and having 9% protein on a dry basis and 84% by weight moisture at a pH 5.4 after heparin extraction) was mixed with porcine red blood cells and water at a ratio of 1.5:1:1.5 (peptone solution:red blood cells:water-weight basis). The pH was adjusted from 5.7 to 7.0 with sodium hydroxide, and the solution was agitated during the adjustment. The solution was then heated to 55° C. for 20 minutes, followed by heating to 65° C. for 15 minutes after which the solution was cooled to about 52° C. Hydrogen peroxide (0.5% w/w of pure hydrogen peroxide, which is equivalent to 1.5% of 34% hydrogen peroxide) was added to the solution as the solution was agitated. The color changed from blood red to a light yellowish color after about 15 minutes. A commercially available bacterial alkaline protease enzyme having a minimum activity of 580,000 DU/g was added to the decolorized solution at a rate of 2 g of enzyme per kg of protein. After mixing for 25 minutes, the protease enzyme was then added to the solution at a rate of 1 g of enzyme per kg of protein. The solution was agitated for 2.5 hours in a tank equipped with a recirculation pump. The product was checked for hydrogen peroxide with 0.01 M $KMnO_4$ against the diluted solution (1:200). There was no hydrogen peroxide remaining in the product. The solution was heated to 90° C. and maintained at this temperature for 10 minutes in order to deactivate the enzyme activity. After the solution was cooled to about 55° C., more peptone and porcine plasma were added at final solid rate 25:25:50 of peptone:red blood cells:plasma. The mixture was then spray dried into a light yellowish powder which had a mild flavor. The analytical data were as follows: protein (76.4%); moisture (5.1%); fat (2.7%); ash (12.5%); pH (6.9); *Salmonella*—negative/25 g sample; *E. Coli*—<3 cfu/g; and Coliforms—<3 cfu/g.

Example 6

Peptone and Whey Protein Concentrate

Peptone solution having a 9% protein content, 84% moisture content, and a of pH 5.4 was obtained from a heparin manufacturer. A whey protein concentrate solution (10% solid) was mixed with the peptone solution at a ratio of 7:3 (whey concentrate:peptone solution-volume basis). The pH was adjusted from 6.0 to 7.8 by adding sodium hydroxide while agitating the solution. The solution was heated to 55° C., and this temperature was maintained for a time period of 3 hours. The solution was then heated to 93° C. and maintained at this temperature for about 5 minutes in order to deactivate the enzymatic activity. The solution was dried in an oven overnight at 93° C. The resulting solid was ground into a light-colored powder which had a nice flavor. The analytical data of the powder were as follows: protein (45.4%); and fat (1.9%) (on a dry basis). As a comparison, whey protein concentrate has a protein content of 38.6% and a fat content of 1.0%, both on a dry basis.

Example 7

Peptone and Fish Offal

Peptone solution having a 9% protein content, an 84% moisture content, and a of pH of 5.4 was obtained from a heparin manufacturer. The peptone solution was mixed with fish offal and water at a ratio of 1:1:1.5 (peptone solution:fish offal:water-weight basis). The solution was then blended with a kitchen blender for about 3 minutes after which the pH was adjusted from 5.8 to 8.0 with sodium hydroxide. A commercially available bacterial alkaline protease enzyme having a minimum activity of 580,000 DU/g was added to the solution at a rate of 0.5 g of enzyme per kg of solid. The solution was then heated to 55° C. where it was maintained for a time period of 3 hours. The solution was blended for 2 minutes after the first hour of this 3 hour period. Sodium hydroxide was again used to readjust the pH to 8.0. After the 3 hour period, the solution was heated to 90° C. for 5 minutes to inactivate the enzymes followed by filtering with a screen having a hole size of 420 Am size. The bones (which could not pass through the screen) were weighed, and the ratio of the bones to fish offal was 16.4% (wet basis), indicating that 83.6% of the fish offal (wet basis) was solubilized. The filtered solution was dried in an oven overnight at 90° C. The resulting solid was ground into a light-colored powder which had a fish flavor. The analytical data of the powder were as follows: protein (61.2%); moisture (5.0%); and fat (9.3%). The bones were then dried in an oven overnight at 90° C. and ground into a light-colored powder.
The analytical data for the bones were as follows: protein (33.9%); fat (1.4%); moisture (3.8%); ash (57.8%); calcium (21.5%); and phosphorus (10.3%).

Example 8

Peptone and Meat Isolate

Peptone solution having a 9% protein content, an 84% moisture content, and a of pH 5.4 was obtained from a heparin manufacturer. Meat isolate solution (with a 10% solids content) was mixed with the peptone solution at a ratio of 3:1 (volume basis). The pH of the solution was adjusted from 5.8 to 7.8 with sodium hydroxide with the solution being agitated during the pH adjustment. The solution was heated to 55° C. and maintained at this temperature for about 3 hours. The solution was then heated to 90° C. and maintained at this temperature for about 5 minutes in order to deactivate the enzymes. The solution was dried in an oven overnight at 93° C. The resulting solid was ground into a light-colored powder. The analytical data of the powder were as follows: protein (78.6%); moisture (7.3%); ash (14.6%); and fat (3.7%).

The invention claimed is:
1. A preserved mucosa tissue product formed by heating a quantity of mucosa from about 50-105° C. and contacting the mucosa tissue with a preserving agent selected from the group consisting of hydrogen peroxide in an amount of less than about 1% weight by weight of mucosal tissue and phosphoric acid in an amount sufficient to reduce the pH of the tissue to about 2 to 4, wherein the preserved mucosal tissue has an ash content of less than about 10% by weight.

2. The product of claim 1 wherein said preserving agent is hydrogen peroxide and the quantity of hydrogen peroxide in said preserved mucosa tissue is less than about 0.04% by weight, based upon the total weight of the preserved mucosa tissue taken as 100% by weight.

3. The product of claim 1 wherein said preserving agent is phosphoric acid and the pH of the preserved mucosa tissue is from about 2-4.

4. The product of claim 1 wherein about seven days after said mucosa tissue is contacted with said preserving agent said preserved mucosa tissue has a standard plate count of less than about 20,000 cfu/g.

5. The product of claim 1 wherein about seven days after said mucosa tissue is contacted with said preserving agent said preserved mucosa tissue has an *E. Coli* count of less than about 10 cfu/g.

* * * * *